(12) United States Patent
Oh et al.

(10) Patent No.: US 11,492,602 B2
(45) Date of Patent: Nov. 8, 2022

(54) M13 MUTANT FOR INCREASING PRODUCTION OF DNA

(71) Applicant: Korea University Research and Business Foundation, Seoul (KR)

(72) Inventors: Min Kyu Oh, Seongnam-si (KR); Dong June Ahn, Seoul (KR); Seungwoo Lee, Seoul (KR); Bo Young Lee, Seoul (KR); Jun Min Lee, Seoul (KR); Jae Won Lee, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 461 days.

(21) Appl. No.: 16/702,194

(22) Filed: Dec. 3, 2019

(65) Prior Publication Data
US 2021/0040455 A1 Feb. 11, 2021

(30) Foreign Application Priority Data
Aug. 7, 2019 (KR) .................... 10-2019-0096197

(51) Int. Cl.
*C12N 7/00* (2006.01)
*C12N 15/63* (2006.01)

(52) U.S. Cl.
CPC .............. *C12N 7/00* (2013.01); *C12N 15/63* (2013.01); *C12N 2795/00021* (2013.01)

(58) Field of Classification Search
None
See application file for complete search history.

(56) References Cited

U.S. PATENT DOCUMENTS 8,969,253 B2 * 3/2015 Reiersen ................ C40B 50/06
506/9
2019/0142882 A1 5/2019 Shepherd et al.

OTHER PUBLICATIONS

Løset, Geir Åge, Bjarne Bogen, and Inger Sandlie. "Expanding the versatility of phage display I: efficient display of peptide-tags on protein VII of the filamentous phage." PloS one 6.2 (2011): e14702. (Year: 2011).*
Communication dated Jan. 21, 2021, issued by the Korean Intellectual Property Office in Korean Application No. 10-2019-0096197.
Tomer A. Roth et al, "A Minimized M13 Coat Protein Defines the Requirements for Assembly into the Bacteriophage Particle", J. Mol. Biol., vol. 322, 2002, pp. 357-367 (11 Pages Total).
Tyson R. Shepherd et al., "Bioproduction of pure, kilobase-scale single-stranded DNA", Scientific Reports, vol. 9., No. 6121, Apr. 2019, pp. 1-9.
Timothy J. Henry et al., "The Proteins of Bacteriophage M13", Genetics: Henry and Pratt, vol. 62, 1969, pp. 800-807 (8 Pages total).
Benjamin Kick, et al., "Efficient Production of Single-Stranded Phage DNA as Scaffolds for DNA Origami", Nano Letters, 2015, pp. 4672-4676, vol. 15.

* cited by examiner

*Primary Examiner* — Weihua Fan
(74) *Attorney, Agent, or Firm* — Sughrue Mion, PLLC

(57) ABSTRACT

The present invention provides a gene including an M13 p5 expressing cassette, which includes a promoter, a ribosome binding site (RBS) and a protein 5 (p5) coding region, wherein at least one base of sequences between the RBS and the p5 coding region is mutated. Using this gene may increase production of single-stranded DNA.

12 Claims, 9 Drawing Sheets
(1 of 9 Drawing Sheet(s) Filed in Color)
Specification includes a Sequence Listing.

[FIG. 1]
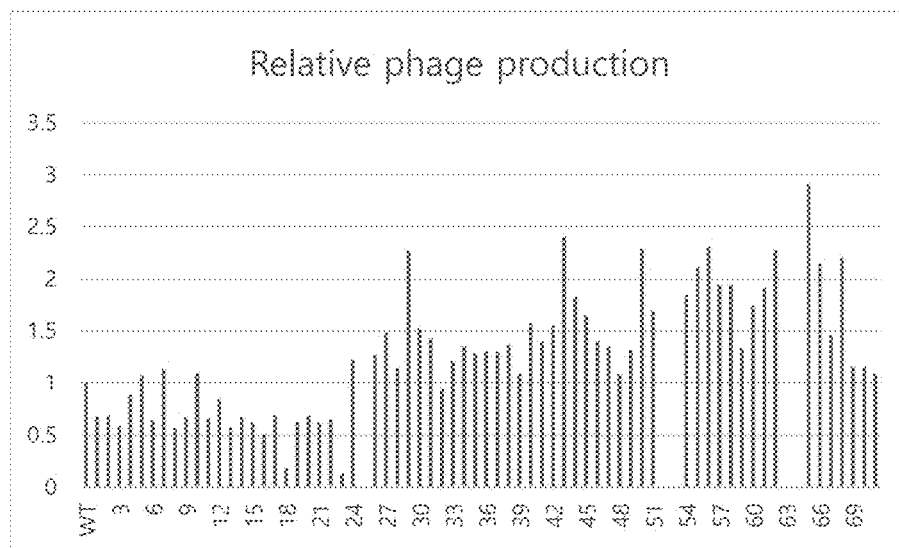

[FIG. 2]
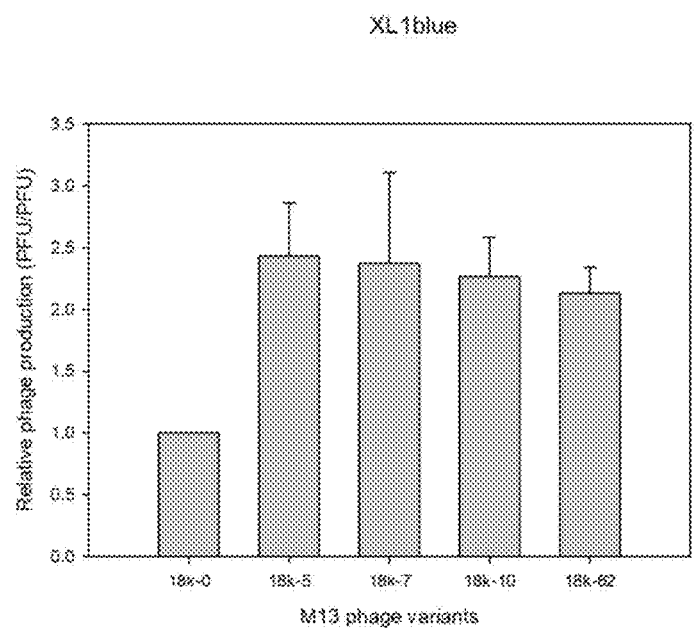
[FIG. 3]
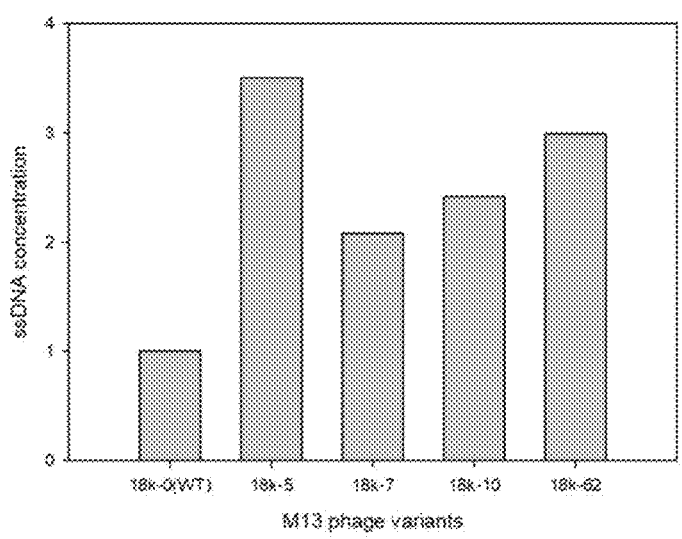

[FIG. 4]

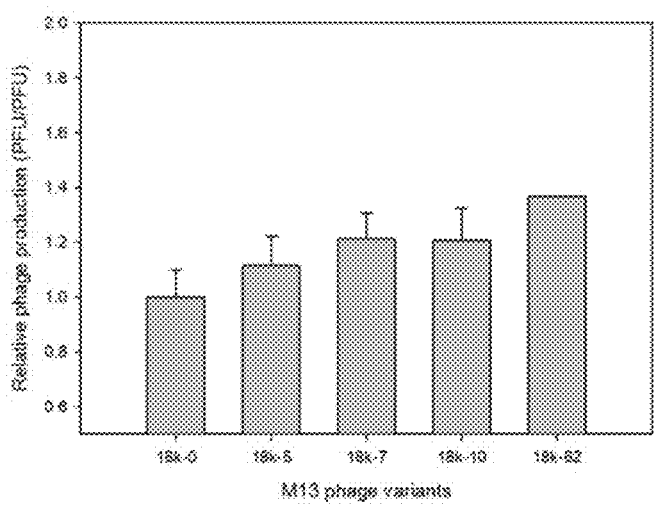

[FIG. 5]

p5 expressing cassette_18k-0

TAACGTAGATTTTTCTTCCCAACGTCCTGACTGGTATAATGAGCCAGTTCTTAAAATCGCATAAGGTAATTCAC
AATGATTAAAGTTGAAATTAAACCATCTCAAGCCCAATTTACTACTCGTTCTGGTGTTTCTCGTCAGGGCAAGC
CTTATTCACTGAATGAGCAGCTTTGTTACGTTGATTTGGGTAATGAATATCCGGTTCTTGTCAAGATTACTCTTGA
TGAAGGTCAGCCAGCCTATGCGCCTGGTCTGTACACCGTTCATCTGTCCTCTTTCAAAGTTGGTCAGTTCGGTT
CCCTTATGATTGACCGTCTGCGCCTCGTTCCGGCTAAGTAA

Promoter region

RBS

Spacer

P5 Coding region

[FIG. 6]

p5 expressing cassette_18k-5

<u>TAACGTAGATTTTTCTTCCCAACGTCCTGACTGGTATAATGAGCCAGTTCTTAAAATCGCATAA</u>GGTAATCTGA
CATGATTAAAGTTGAAATTAAACCATCTCAAGCCCAATTTACTACTCGTTCTGGTGTTTCTCGTCAGGGCAAGC
CTTATTCACTGAATGAGCAGCTTTGTTACGTTGATTTGGGTAATGAATATCCGGTTCTTGTCAAGATTACTCTTGA
TGAAGGTCAGCCAGCCTATGCGCCTGGTCTGTACACCGTTCATCTGTCCTCTTTCAAAGTTGGTCAGTTCGGTT
CCCTTATGATTGACCGTCTGCGCCTCGTTCCGGCTAAGTAA

<u>Promoter region</u>

RBS

<u>Spacer</u>

*P5 Coding region*

[FIG. 7]

p5 expressing cassette_18k-7

<u>TAACGTAGATTTTTCTTCCCAACGTCCTGACTGGTATAATGAGCCAGTTCTTAAAATCGCATAA</u>GGTAATTCGTA
*ATGATTAAAGTTGAAATTAAACCATCTCAAGCCCAATTTACTACTCGTTCTGGTGTTTCTCGTCAGGGCAAGCCT*
*TATTCACTGAATGAGCAGCTTTGTTACGTTGATTTGGGTAATGAATATCCGGTTCTTGTCAAGATTACTCTTGATG*
*AAGGTCAGCCAGCCTATGCGCCTGGTCTGTACACCGTTCATCTGTCCTCTTTCAAAGTTGGTCAGTTCGGTTCC*
*CTTATGATTGACCGTCTGCGCCTCGTTCCGGCTAAGTAA*

<u>Promoter region</u>

RBS

<u>Spacer</u>

*P5 Coding region*

[FIG. 8]

p5 expressing cassette_18k-10

TAACGTAGATTTTTCTTCCCAACGTCCTGACTGGTATAATGAGCCAGTTCTTAAAATCGCATAAGGTAATTCTTC
ATGATTAAAGTTGAAATTAAACCATCTCAAGCCCAATTTACTACTCGTTCTGGTGTTTCTCGTCAGGGCAAGCCT
TATTCACTGAATGAGCAGCTTTGTTACGTTGATTTGGGTAATGAATATCCGGTTCTTGTCAAGATTACTCTTGATG
AAGGTCAGCCAGCCTATGCGCCTGGTCTGTACACCGTTCATCTGTCCTCTTTCAAAGTTGGTCAGTTCGGTTCC
CTTATGATTGACCGTCTGCGCCTCGTTCCGGCTAAGTAA

Promoter region

RBS

Spacer

*P5 Coding region*

[FIG. 9]

p5 expressing cassette_18k-62

TAACGTAGATTTTTCTTCCCAACGTCCTGACTGGTATAATGAGCCAGTTCTTAAAATCGCATAAGGTAATGAGG
TATGATTAAAGTTGAAATTAAACCATCTCAAGCCCAATTTACTACTCGTTCTGGTGTTTCTCGTCAGGGCAAGCC
TTATTCACTGAATGAGCAGCTTTGTTACGTTGATTTGGGTAATGAATATCCGGTTCTTGTCAAGATTACTCTTGAT
GAAGGTCAGCCAGCCTATGCGCCTGGTCTGTACACCGTTCATCTGTCCTCTTTCAAAGTTGGTCAGTTCGGTTC
CCTTATGATTGACCGTCTGCGCCTCGTTCCGGCTAAGTAA

Promoter region

RBS

Spacer

*P5 Coding region*

```
GTACCCGGGGATCCTCTAGAGTCGACCTGCAGGCATGCAAGCTTGGCACTGGCCGTCGTTTTACAACGTCGTGACTGGGAA
AACCCTGGCGTTACCCAACTTAATCGCCTTGCAGCACATCCCCCTTTCGCCAGCTGGCGTAATAGCGAAGAGGCCCGCACCG
ATCGCCCTTCCCAACAGTTGCGCAGCCTGAATGGCGAATGGCGCTTTGCCTGGTTTCCGGCACCAGAAGCGGTGCCGGAAA
GCTGGCTGGAGTGCGATCTTCCTGAGGCCGATACTGTCGTCGTCCCCTCAAACTGGCAGATGCACGGTTACGATGCGCCCAT
CTACACCAACGTGACCTATCCCATTACGGTCAATCCGCCGTTTGTTCCCACGGAGAATCCGACGGGTTGTTACTCGCTCACAT
TTAATGTTGATGAAAGCTGGCTACAGGAAGGCCAGACGCGAATTATTTTTGATGGCGTTCCTATTGGTTAAAAAATGAGCTG
ATTTAACAAAAATTTAATGCGAATTTTAACAAAATATTAACGTTTACAATTTAAATATTTGCTTATACAATCTTCCTGTTTTTGGG
GCTTTTCTGATTATCAACCGGGGTACATATGATTGACATGCTAGTTTTACGATTACCGTTCATCGATTCTCTTGTTGCTCCAGA
CTCTCAGGCAATGACCTGATAGCCTTTGTAGATCTCTCAAAAATAGCTACCCTCTCCGGCATTAATTTATCAGCTAGAACGGTT
GAATATCATATTGATGGTGATTTGACTGTCTCCGGCCTTTCTCACCCTTTTGAATCTTTACCTACACATTACTCAGGCATTGCATT
TAAAATATATGAGGGTTCTAAAAATTTTTATCCTTGCGTTGAAATAAAGGCTTCTCCCGCAAAAGTATTACAGGGTCATAATGT
TTTTGGTACAACCGATTTAGCTTTATGCTCTGAGGCTTTATTGCTTAATTTTGCTAATTCTTTGCCTTGCCTGTATGATTTATTGG
ATGTTAATGCTACTACTATTAGTAGAATTGATGCCACCTTTTCAGCTCGCGCCCCAAATGAAAATATAGCTAAACAGGGTATTGA
CCATTTGCGAAATGTATCTAATGGTCAAACTAAATCTACTCGTTCGCAGAATTGGGAATCAACTGTTATATGGAATGAAACTTC
CAGACACCGTACTTTAGTTGCATATTTAAAACATGTTGAGCTACAGCATATATTCAGCAATTAAGCTCTAAGCCATCCGCAAA
AATGACCTCTTATCAAAAGGAGCAATTAAAGGTACTCTCTAATCCTGACCTGTTGGAGTTTGCTTCCGGTCTGGTTCGCTTTG
AAGCTCGAATTAAAACGCGATATTTGAAGTCTTTCGGGCTTCCTCTTAATCTTTTTGATGCAATCCGCTTTGCTTCTGACTATAA
TAGTCAGGGTAAAGACCTCATTTTTGATTTATGGTCATTCTCGTTTTCTGAACTGTTTAAAGCATTTGAGGGGGATTCAATGA
ATATTTATGACGATTCCGCAGTATTGGACGCTATCCAGTCTAAACATTTTACTATTACCCCCTCTGGCAAAACTTCTTTTGCAAA
AGCCCTCTCGCTATTTTGGTTTTTATCGTCGTCTGGTAAACGAGGGTTATGATAGTGTTGCTCTTACTATGCCTCGTAATTCCTTT
TGGCGTTATGTATCTGCATTAGTTGAATGTGGTATTCCTAAATCTCAACTGATGAATCTTTCTACCTGTAATAATGTTGTTCCGTT
AGTTCGTTTTATTAACGTAGATTTTTCTTCCCAACGTCCTGACTGGTATAATGAGCCAGTTCTTAAAATCGCATAAGGTAATTC
ACAATGATTAAAGTTGAAATTAAACCATCTCAAGCCCAATTTACTACTCGTTCTGGTGTTTCTCGTCAGGGCAAGCCTTATTCA
CTGAATGAGCAGCTTTGTTACGTTGATTTGGGTAATGAATATCCGGTTCTTGTCAAGATTACTCTTGATGAAGGTCAGCCAGCC
TATGCGCCTGGTCTGTACACCGTTCATCTGTCCTCTTTCAAAGTTGGTCAGTTCGGTTCCCTTATGATTGACCGTCTGCGCCTCG
TTCCGGCTAAGTAACATGGAGCAGGTCGCGGATTTCGACACAATTTATCAGGCGATGATACAAATCTCCGTTGTACTTTGTTT
CGCGCTTGGTATAATCGCTGGGGGTCAAAGATGAGTGTTTTAGTGTATTCTTTTGCCTCTTTCGTTTTAGGTTGGTGCCTTCGT
AGTGGCATTACGTATTTTACCCGTTTAATGGAAACTTCCTCATGAAAAAGTCTTTAGTCCTCAAAGCCTCTGTAGCCGTTGCTA
CCCTCGTTCCGATGCTGTCTTTCGCTGCTGAGGGTGACGATCCCGCAAAAGCGGCCTTTAACTCCCTGCAAGCCTCAGCGAC
CGAATATATCGGTTATGCGTGGGCGATGGTTGTTGTCATTGTCGGCGCAACTATCGGTATCAAGCTGTTTAAGAAATTCACCTC
GAAAGCAAGCTGATAAACCGATACAATTAAAGGCTCCTTTTGGAGCCTTTTTTTTGGAGATTTTCAACGTGAAAAAATTATTA
TTCGCAATTCCTTTAGTTGTTCCTTTCTATTCTCACTCCGCTGAAACTGTTGAAAGTTGTTTAGCAAAATCCCATACAGAAAATT
CATTTACTAACGTCTGGAAAGACGACAAAACTTTAGATCGTTACGCTAACTATGAGGGCTGTCTGTGGAATGCTACAGGCGTT
GTAGTTTGTACTGGTGACGAAACTCAGTGTTACGGTACATGGGTTCCTATTGGGCTTGCTATCCCTGAAAATGAGGGTGGTG
GCTCTGAGGGTGGCGGTTCTGAGGGTGGCGGTTCTGAGGGTGGCGGTACTAAACCTCCTGAGTACGGTGATACACCTATTC
CGGGCTATACTTATATCAACCCTCTCGACGGCACTTATCCGCCTGGTACTGAGCAAAACCCCGCTAATCCTAATCCTTCTCTTGA
GGAGTCTCAGCCTCTTAATACTTTCATGTTTCAGAATAATAGGTTCCGAAATAGGCAGGGGGCATTAACTGTTTATACGGGCA
CTGTTACTCAAGGCACTGACCCCGTTAAAACTTATTACCAGTACACTCCTGTATCATCAAAAGCCATGTATGACGCTTACTGGA
ACGGTAAATTCAGAGACTGCGCTTTCCATTCTGGCTTTAATGAGGATTTATTTGTTTGTGAATATCAAGGCCAATCGTCTGACC
TGCCTCAACCTCCTGTCAATGCTGGCGGCGGCTCTGGTGGTGGTTCTGGTGGCGGCTCTGAGGGTGGTGGCTCTGAGGGTG
GCGGTTCTGAGGGTGGCGGCTCTGAGGGAGGCGGTTCCGGTGGTGGCTCTGGTTCCGGTGATTTTGATTATGAAAAGATG
GCAAACGCTAATAAGGGGGCTATGACCGAAAATGCCGATGAAAACGCGCTACAGTCTGACGCTAAAGGCAAACTTGATTCT
GTCGCTACTGATTACGGTGCTGCTATCGATGGTTTCATTGGTGACGTTTCCGGCCTTGCTAATGGTAATGGTGCTACTGGTGAT
TTTGCTGGCTCTAATTCCCAAATGGCTCAAGTCGGTGACGGTGATAATTCACCTTTAATGAATAATTTCCGTCAATATTTACCTT
CCCTCCCTCAATCGGTTGAATGTCGCCCTTTTGTCTTTGGCGCTGGTAAACCATATGAATTTTCTATTGATTGTGACAAAATAA
ACTTATTCCGTGGTGTCTTTGCGTTTCTTTTATATGTTGCCACCTTTATGTATGTATTTTCTACGTTTGCTAACATACTGCGTAATA
AGGAGTCTTAATCATGCCAGTTCTTTTGGGTATTCCGTTATTATTGCGTTTCCTCGGTTTCCTTCTGGTAACTTTGTTCGGCTAT
CTGCTTACTTTTCTTAAAAAGGGCTTCGGTAAGATAGCTATTGCTATTTCATTGTTTCTTGCTCTTATTATTGGGCTTAACTCAAT
TCTTGTGGGTTATCTCTCTGATATTAGCGCTCAATTACCCTCTGACTTTGTTCAGGGTGTTCAGTTAATTCTCCCGTCTAATGCG
CTTCCCTGTTTTTATGTTATTCTCTCTGTAAAGGCTGCTATTTTCATTTTTGACGTTAAACAAAAAATCGTTTCTTATTTGGATTG
```

[FIG. 10b]

```
GGATAAATAATATGGCTGTTTATTTTGTAACTGGCAAATTAGGCTCTGGAAAGACGCTCGTTAGCGTTGGTAAGATTCAGGAT
AAAATTGTAGCTGGGTGCAAAATAGCAACTAATCTTGATTTAAGGCTTCAAAACCTCCCGGCAAGTCGGGAGGTTCGCTAAAA
CGCCTCGCGTTCTTAGAATACCGGATAAGCCTTCTATATCTGATTTGCTTGCTATTGGGCGCGGTAATGATTCCTACGATGAAA
ATAAAAACGGCTTGCTTGTTCTCGATGAGTGCGGTACTTGGTTTAATACCCGTTCTTGGAATGATAAGGAAAGACAGCCGATT
ATTGATTGGTTTCTACATGCTCGTAAATTAGGATGGGATATTATTTTTCTTGTTCAGGACTTATCTATTGTTGATAAACAGGCGC
GTTCTGCATTAGCTGAACATGTTGTTTATTGTCGTCGTCTGGACAGAATTACTTTACCTTTTGTCGGTACTTTATATTCTCTTATT
ACTGGCTCGAAAATGCCTCTGCCTAAATTACATGTTGGCGTTGTTAAATATGGCGATTCTCAATTAAGCCCTACTGTTGAGCGT
TGGCTTTATACTGGTAAGAATTTGTATAACGCATATGATACTAAACAGGCTTTTTCTAGTAATTATGATTCCGGTGTTTATTCTTA
TTTAACGCCTTATTTATCACACGGTCGGTATTTCAAACCATTAAATTTAGGTCAGAAGATGAAATTAACTAAAATATATTTGAAA
AAGTTTTCTCGCGTTCTTTGTCTTGCGATTGGATTTGCATCAGCATTTACATATAGTTATATAACCCAACCTAAGCCGGAGGTTA
AAAAAGGTAGTCTCTCAGACCTATGATTTTGATAAAATTCACTATTGACTCTTCTCAGCGGTCTTAATCTAAGCTATCGCTATGTTTTC
AAGGATTCTAAGGGAAAATTAATTAATAGCGACGATTTACAGAAGCAAGGTTATTCACTCACATATATTGATTTATGTACTGTT
TCCATTAAAAAAGGTAATTCAAATGAAATTGTTAAATGTAATTAATTTTGTTTTTCTTGATGTTTGTTTCATCATCTTCTTTTGCTC
AGGTAATTGAAATGAATAATTCGCCTCTGCGCGATTTTGTAACTTGGTATTCAAAGCAATCAGGCGAATCCGTTATTGTTTCTC
CCGATGTAAAAGGTACTGTTACTGTATATTCATCTGACGTTAAACCTGAAAATCTACGCAATTTCTTTATTTCTGTTTTACGTGC
AAATAATTTTGATATGGTAGGTTCTAACCCTTCCATTATTCAGAAGTATAATCCAAACAATCAGGATTATATTGATGAATTGCCAT
CATCTGATAATCAGGAATATGATGATAATTCCGCTCCTTCTGGTGGTTTCTTTGTTCCGCAAAATGATAATGTTACTCAAACTTT
TAAAATTAATAACGTTCGGGCAAAGGATTTAATACGAGTTGTCGAATTGTTTGTAAAGTCTAATACTTCTAAATCCTCAAATGT
ATTATCTATTGACGGCTCTAATCTATTAGTTGTTAGTGCTCCTAAAGATATTTAGATAACCTTCCTCAATTCCTTTCAACTGTTG
ATTTGCCAACTGACCAGATATTGATTGAGGGTTTGATATTTGAGGTTCAGCAAGGTGATGCTTTAGATTTTTCATTTGCTGCTG
GCTCTCAGCGTGGCACTGTTGCAGGCGGTGTTAATACTGACCGCCTCACCTCTGTTTTATCTTCTGCTGGTGGTTCGTTCGGT
ATTTTTAATGGCGATGTTTTAGGGCTATCAGTTCGCGCATTAAAGACTAATAGCCATTCAAAAATATTGTCTGTGCCACGTATTC
TTACGCTTTCAGGTCAGAAGGGTTCTATCTCTGTTGGCCAGAATGTCCCTTTTATTACTGGTCGTGTGACTGGTGAATCTGCC
AATGTAAATAATCCATTTCAGACGATTGAGCGTCAAAATGTAGGTATTTCCATGAGCGTTTTCCTGTTGCAATGGCTGGCGG
TAATATTGTTCTGGATATTACCAGCAAGGCCGATAGTTTGAGTTCTTCTACTCAGGCAAGTGATGTTATTACTAATCAAAGAAG
TATTGCTACAACGGTTAATTGCGTGATGGACAGACTCTTTACTCGGTGACCTCACTGATTATAAAAACACTTCTCAGGATTC
TGGCGTACCGTTCCTGTCTAAAATCCCTTTAATCGGCCTCCTGTTTAGCTCCCGCTCTGATTCTAACGAGGAAAGCACGTTATA
CGTGCTCGTCAAAAGCAACCATAGTACGCGCCCTGTAGCGGCGCATTAAGCGCGGCGGGTGTGGTGGTTACGCGCAGCGTGA
CCGCTACACTTGCCAGCGCCCTAGCGCCCGCTCCTTTCGCTTTCTTCCCTTCCTTTCTCGCCACGTTCGCCGGCTTTCCCCGTC
AAGCTCTAAATCGGGGGCTCCCTTTAGGGTTCCGATTTAGTGCTTTACGGCACCTCGACCCCAAAAAACTTGATTTGGGTGA
TGGTTCACGTAGTGGGCCATCGCCCTGATAGACGGTTTTTCGCCCTTTGACGTTGGAGTCCACGTTCTTTAATAGTGGACTCT
TGTTCCAAACTGGAACAACACTCAACCCTATCTCGGGCTATTCTTTTTGATTTATAAGGGATTTTGCCGATTTCGGAACCACCAT
CAAACAGGATTTTCGCCTGCTGGGGCAAACCAGCGTGGACCGCTTGCTGCAACTCTCTCAGGGCCAGGCGGTGAAGGGCA
ATCAGCTGTTGCCCGTCTCACTGGTGAAAAGAAAAACCACCCTGGCGCCCAATACGCAAACCGCCTCTCCCCGCGCGTTGGC
CGATTCATTAATGCAGCTGGCACGACAGGTTTCCCGACTGGAAAGCGGGCAGTGAGCGCAACGCAATTAATGTGAGTTAGC
TCACTCATTAGGCACCCCAGGCTTTACACTTTATGCTTCCGGCTCGTATGTTGTGTGGAATTGTGAGCGGATAACAATTTCACA
CAGGAAACAGCTATGACCATGATTACGAAGATCCCCTCACGCTGCCGCAAGCACTCAGGGCGCAAGGGCTGCTAAAGGAA
GCGGAACACGTAGAAAGCCAGTCCGCAGAAACGGTGCTGACCCCGGATGAATGTCAGCTACTGGGCTATCTGGACAAGGG
AAAACGCAAGCGCAAAGAGAAAGCAGGTAGCTTGCAGTGGGCTTACATGGCGATAGCTAGACTGGGCGGTTTTATGGACA
GCAAGCGAACCGGAATTGCCAGCTGGGGCGCCCTCTGGTAAGGTTGGGAAGCCCTGCAAAGTAAACTGGATGGCTTTCTT
GCCGCCAAGGATCTGATGGCGCAGGGGATCAAGATCTGATCAAGAGACAGGATGAGGATCGTTTCGCATGATTGAACAAGA
TGGATTGCACGCAGGTTCTCCGGCCGCTTGGGTGGAGAGGCTATTCGGCTATGACTGGGCACAACAGACAATCGGCTGCTC
TGATGCCGCCGTGTTCCGGCTGTCAGCGCAGGGGCGCCCGGTTCTTTTTGTCAAGACCGACCTGTCCGGTGCCCTGAATGA
ACTGCAGGACGAGGCAGCGCGGCTATCGTGGCTGGCCACGACGGGCGTTCCTTGCGCAGCTGTGCTCGACGTTGTCACTG
AAGCGGGAAGGGACTGGCTGCTATTGGGCGAAGTGCCGGGGCAGGATCTCCTGTCATCTCACCTTGCTCCTGCCGAGAAA
GTATCCATCATGGCTGATGCAATGCGGCGGCTGCATACGCTTGATCCGGCTACCTGCCCATTCGACCACCAAGCGAAACATCG
CATCGAGCGAGCACCTGTACTCGGATGGAAGCCGGTCTTGTCGATCAGGATGATCTGGACGAAGAGCATCAGGGGCTCGCGC
CAGCCGAACTGTTCGCCAGGCTCAAGGCGCGCATGCCCGACGGCGAGGATCTCGTCGTGACCCATGGCGATGCCTGCTTGC
CGAATATCATGGTGGAAAATGGCCGCTTTTCTGGATTCATCGACTGTGGCCGGCTGGGTGTGGCGGACCGCTATCAGGACAT
AGCGTTGGCTACCCGTGATATTGCTGAAGAGCTTGGCGGCGAATGGGCTGACCGCTTCCTCGTGCTTTACGGTATCGCCGCT
CCCGATTCGCAGCGCATCGCCTTCTATCGCCTTCTTGACGAGTTCTTCTGAGCGGGACTCTGGGGTTCGAAATGACCGACCA
AGCGACGCCCAACCTGCCATCACGAGATTTCGATTCCACCGCCGCCTTCTATGAAAGGTTGGGCTTCGGAATCGTTTTCCGG
```

[FIG. 10c]

GACGCCGGCTGGATGATCCTCCAGCGCGGGATCTCATGCTGGAGTTCTTCGCCCACCCCAGCTTCAAAAGCGCTCT

Promoter region

RBS

Spacer

P5 Coding region

[FIG. 11]

| Phage | Spacer sequence | | Phage | Spacer sequence |
|---|---|---|---|---|
| 18k-0 | TCACA | | 18k-37 | TTTAA |
| 18k-1 | GTCTT | | 18k-38 | GTGTC |
| 18k-2 | TATTA | | 18k-39 | AAGGA |
| 18k-3 | CTCTA | | 18k-40 | AAGTA |
| 18k-4 | TGGAT | | 18k-41 | TGCTA |
| 18k-5 | CTGAC | | 18k-42 | ATGGT |
| 18k-6 | CATTC | | 18k-43 | CGTTA |
| 18k-7 | TCGTA | | 18k-44 | GTGAA |
| 18k-8 | GTTCT | | 18k-45 | GAAAT |
| 18k-9 | GCATT | | 18k-46 | AGGTT |
| 18k-10 | TCTTC | | 18k-47 | GTGTA |
| 18k-11 | CGGT | | 18k-48 | GACTC |
| 18k-12 | CGGC | | 18k-49 | ATTCG |
| 18k-13 | TTATT | | 18k-50 | TAATT |
| 18k-14 | GCAGT | | 18k-51 | CATGA |
| 18k-15 | TATTT | | 18k-52 | TCTTA |
| 18k-16 | ACACA | | 18k-53 | TTTTT |
| 18k-17 | GATTG | | 18k-54 | GCTAA |
| 18k-18 | AAGTC | | 18k-55 | GTTTT |
| 18k-19 | CGTAA | | 18k-56 | ATGCT |
| 18k-20 | CTGGC | | 18k-57 | CAGTT |
| 18k-21 | ATGGA | | 18k-58 | TACTA |
| 18k-22 | CAGGC | | 18k-59 | AGCCA |
| 18k-23 | CGGGC | | 18k-60 | CCCTC |
| 18k-24 | TTGTA | | 18k-61 | CACTA |
| 18k-25 | TCGTT | | 18k-62 | GAGGT |
| 18k-26 | CCAAC | | 18k-63 | AACAA |
| 18k-27 | TGTAT | | 18k-64 | TTAGG |
| 18k-28 | GAGTA | | 18k-65 | GAGTT |
| 18k-29 | AGTAT | | 18k-66 | CGATC |
| 18k-30 | TTGTC | | 18k-67 | CACAG |
| 18k-31 | GTTTA | | 18k-68 | TTTTG |
| 18k-32 | CCGGC | | 18k-69 | TTTGA |
| 18k-33 | ATCGA | | 18k-70 | CGGTA |
| 18k-34 | GTTGT | | 18k-71 | GATTT |
| 18k-35 | TTTTA | | | |
| 18k-36 | TGTCT | | | |

M13 MUTANT FOR INCREASING PRODUCTION OF DNA

BACKGROUND OF THE INVENTION

1. Field of the Invention

The present invention relates to an M13 mutant for increasing production of DNA.

2. Description of the Related Art

In order to produce DNA origami, a great amount of single-stranded DNA molecules in a gram level is required. However, according to typical DNA synthesis methods such as PCR, a method for separation of biotinylated strands using streptavidin beads, a method for degradation of a single phosphorylated strand using lambda (A) nuclease, length-dependent separation through urea-modified polyacrylamide gel electrophoresis, circular template rolling circle type replication, a process of cutting a single strand of plasmid then sequentially degrading the same, etc., only DNAs in μg or mg level are produced.

Further, it is known that DNA can be produced using non-lytic bacteriophage M13, wherein 1 to 14 mg/L of single-stranded DNAs are prepared (Sambrook, J.; Fritsch, E. F.; Maniatis, T. Molecular cloning. A laboratory manual, 3rd ed.; Cold Spring Harbor Laboratory Press: Cold Spring Harbor, N.Y., 2001; Bellot, G.; McClintock, M. A.; Chou, J. J.; Shih, W. M. Nat. Protoc 2013, 8 (4), 755-770 DOI: 10.1038/nprot.2013.037.). In order to overcome the limitation in production of the single-stranded DNAs, Benjamin Kick, et al. (Efficient Production of Single-Stranded Phage DNA as Scaffolds for DNA Origami, Nano letters, 2015, 15, 4672-4676) has introduced that DNA production may be increased by about 2 times by regulating incubation conditions such as pH, dissolved oxygen and substrate feed, etc., as compared to the prior art.

However, there is still a need for novel methods capable of efficiently producing higher level of DNAs.

PRIOR ART DOCUMENT

Patent Document

Non-Patent Document

Benjamin Kick, et al., Efficient Production of Single-Stranded Phage DNA as Scaffolds for DNA Origami, Nano letters, 2015, 15, 4672-4676

SUMMARY OF THE INVENTION

An object of the present invention is to provide a method for increasing DNA production by mutating a gene of M13 bacteriophage.

Another object of the present invention is to provide a bacteriophage able to increase production of DNA, or a gene or vector including the same.

In addition, another object of the present invention is to provide a host cell with improved DNA production.

To achieve the above objects, the technical solutions adopted by the present invention are as follows:

1. A gene including: an M13 p5 expressing cassette which includes a promoter, a ribosome binding site (RBS) and a protein 5 (p5) coding region, wherein at least one of sequences between the RBS and the p5 coding region is mutated.

2. The gene according to the above 1, wherein the sequence between the RBS and the p5 coding region is substituted by any one sequence of SEQ ID NO. 6 to SEQ ID NO. 9.

3. The gene according to the above 1, wherein the RBS sequence is represented by SEQ ID NO. 3, and the p5 coding region is represented by SEQ ID NO. 4.

4. The gene according to the above 1, wherein the p5 expressing cassette includes a sequence represented by any one sequence of SEQ ID NO. 10 to SEQ ID NO. 13.

5. An M13 bacteriophage including the gene according to the above 1.

6. A host cell including the gene according to the above 1.

7. A host cell infected with the M13 bacteriophage according to the above 5.

8. The host cell according to the above 6 or 7, wherein the host cell expresses F cilia.

9. A method for increasing production of DNA, including: mutating at least one base of sequences between a ribosome binding site (RBS) and a protein 5 (p5) coding region in an M13 p5 expressing cassette which includes a promoter in M13 bacteriophage, the RBS and the p5 coding region; and infecting a host cell with the mutated M13 bacteriophage.

10. The method according to the above 9, wherein the sequence between the RBS and the p5 coding region is substituted by any one sequence of SEQ ID NO. 6 to SEQ ID NO. 9.

11. The method according to the above 9, wherein the RBS sequence is represented by SEQ ID NO. 3, and the p5 coding region is represented by SEQ ID NO. 4.

12. The method according to the above 9, wherein the p5 expressing cassette includes a sequence represented by any one sequence of SEQ ID NO. 10 to SEQ ID NO. 13.

13. The method according to the above 9, wherein the host cell expresses F cilia.

According to the inventive method, DNA production may be increased as compared to the prior art.

The bacteriophage, or the gene or vector including the same may be introduced into a host cell to increase DNA production, as compared to the prior art.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other objects, features and other advantages of the present invention will be more clearly understood from the following detailed description taken in conjunction with the accompanying drawings, in which:

FIG. 1 is a graph illustrating a ratio of production of bacteriophage by DNA sequence mutation to native (wild type) one according to one embodiment of the present invention;

FIG. 2 is a graph illustrating production of bacteriophage to native one in the mutated spacer sequence-introduced XL1blue strain according to one embodiment of the present invention: 18k-0, 18k-5, 18k-7, 18k-10 and 18k-62 in this order from the left side;

FIG. 3 is a graph illustrating production of single-stranded DNA to native one in the mutated spacer sequence-introduced XL1blue strain according to one embodiment of the present invention: 18k-0, 18k-5, 18k-7, 18k-10 and 18k-62 in this order from the left side;

FIG. 4 is a graph illustrating production of single-stranded DNA to native one in the mutated spacer sequence-introduced Jude1 DH10B F' strain according to one embodiment of the present invention: 18k-0, 18k-5, 18k-7, 18k-10 and 18k-62 in this order from the left side;

FIG. 5 illustrates DNA sequence of p5 protein expressing cassette in the native M13M13mp18k (18k-0) according to one embodiment of the present invention;

FIG. 6 illustrates DNA sequence of p5 protein expressing cassette in M13M13mp18k mutant (18k-5) having a spacer sequence mutated into CTGAC according to one embodiment of the present invention;

FIG. 7 illustrates DNA sequence of p5 protein expressing cassette in M13M13mp18k mutant (18k-7) having a spacer sequence mutated into TCGTA according to one embodiment of the present invention;

FIG. 8 illustrates DNA sequence of p5 protein expressing cassette in M13M13mp18k mutant (18k-10) having a spacer sequence mutated into TCTTC according to one embodiment of the present invention;

FIG. 9 illustrates DNA sequence of p5 protein expressing cassette in M13M13mp18k mutant (18k-62) having a spacer sequence mutated into GAGGT according to one embodiment of the present invention;

FIGS. 10(a), 10(b) and 10(c) illustrate the full-length DNA sequence of the native M13M13mp18k according to one embodiment of the present invention; and FIG. 11 illustrates a spacer sequence, and a spacer mutant sequence of the native M13mp18k (18k-0) according to one embodiment of the present invention.

DETAILED DESCRIPTION OF THE INVENTION

Hereinafter, the present invention will be described in more detail with reference to the accompanying drawings. However, some embodiment of the present invention, but not limited thereto, are illustrated. In fact, these invention may be practically embodied in various formed and should not be construed to limit the present invention to the embodiments proposed in the present disclosure. Singular forms used in the specification and appended claims may also include plural forms unless otherwise specifically indicated.

M13 phage is a fibrous phage infecting *E. coli* through F cilia. When the M13 phage enters *E. coli* having F cilia, M13 DNA is replicated by itself using an enzyme such as DNA polymerase, RNA polymerase and ligase in a host cell. This process is known to rolling circle replication.

The rolling circle replication includes three stages. That is, stage 1 includes infection and formation of replication form (RF). When an M13 template (+) strand enters a cytoplasm, a complementary (−) strand corresponding to the (+) strand is formed. Thereafter, DNA gyrase of *E. coli* forms super-coiled double-stranded M13 DNA (RF). In stage 2, the phage protein, p2, cuts off the (+) strand of RF. 3' hydroxyl group acts as a primer of DNA polymerase and synthesizes (+) strand using a fresh (−) strand as a template. After forming a complete (+) strand, p2 cuts off the (+) strand and divides the (+) strands. As such, a single RF DNA and a single (+) strand may be formed. In this stage, a protein 5 (p5) acts as a regulator. When a concentration of p5 is high, the process may go on stage 3. If the concentration of p5 is low, stage 2 may be repeated. Lastly, stage 3 is a releasing step. When the concentration of p5 is sufficiently high, thousands of p5s are bound to the single (+) strand prepared in stage 2 to form (+) strand-p5 dimer. The dimer acts as a releasing signal and may be released by a transporter including phage proteins, p1, p4 and p11. When the dimer passes through the transporter, p5 is removed and several replicated p3, p6, p7, p8 and p9 are combined with (+) single-stranded DNA to form a phage capsid.

Supposing that a replication rate is constant, the single-stranded DNA (ssDNA) is increased by Fibonacci series in stage 2 while being increased arithmetically in stage 3:

DNA Increase Series in Stage 2

$$\frac{1}{\sqrt{5}}\left(\left(\frac{1+\sqrt{5}}{2}\right)^n - \left(\frac{1-\sqrt{5}}{2}\right)^n\right)$$

DNA Increase Series in Stage 3

$$\frac{1}{\sqrt{5}}\left(\left(\frac{1+\sqrt{5}}{2}\right)^n - \left(\frac{1-\sqrt{5}}{2}\right)^n\right)*x$$

In the above equations, n is the number of repeating the circle, and x is the number of (+) stranded DNA prepared in stage 2.

In order to amplify the production of single-stranded DNAs, the present invention has been developed on the basis of an assumption that it is preferable to maintain stage 2 for a long period of time. In the rolling circle replication, p5 concentration becomes a turning point. If p5 is rapidly accumulated, the process may quickly go on stage 3. On the other hand, if p5 is slowly accumulated, the process may be slowly advanced to stage 3 to thus produce many more single-stranded DNAs.

The present inventors have intended to control accumulation of p5 during translation, and for this purpose, conducted mutation of a ribosome binding site (RBS), a spacer sequence and N-terminal sequence to regulate p5 expression level. As used herein, the term "spacer sequence" refers to a base sequence between the RBS and an initiating codon. The present inventors have expected p5 expression levels of total 71 genes on the upstream of the initiating codon among the p5 expressing cassettes, and based on this expectation, prepared four (4) expressing cassettes. Phage production and DNA production were determined to be increased when the spacer sequence is mutated, thereby the present invention has been completed on the basis of the determination.

The native spacer sequence consists of five (5) nucleic acids (TCACA, SEQ ID NO. 5) and may be mutated according to any method well known in the related art. For instance, position designating mutation or random mutation may be used, and the random mutation may include methods such as error-prone PCR, rolling circle error-prone PCR, use of mutation-deriving strain, use of 'constitutive' mutation-deriving strain, insert mutation production, use of ethyl methane sulfonate, use of nitrous acid, DNA shuffling, production of dNTP-mutant, or the like, but it is not limited thereto.

The spacer sequence may have one, two, three, four or five mutated nucleotides and, when 2 to 4 nucleotides are mutated, the mutated sequence may include continuous nucleotide, partially discontinuous nucleotide or entirely discontinuous nucleotide. For instance, such mutated spacer sequence may include GTCTT, TATTA, CTCTA, TGGAT, CTGAC, CATTC, TCGTA, GTTCT, GCATT, TCTTC, CGGT, CGGC, TATTT, GCAGT, TATTT, ACACA, GATTG, AAGTC, CGTAA, CTGGC, ATGGA, CAGGC, CGGGC, TTGTA, TCGTT, CCAAC, TGTAT, GAGTA, AGTAT, TTGTC, GTTTA, CCGGC, ATCGA, GTTGT, TTTTA, TGTCT, TTTAA, GTGTC, AAGGA, AAGTA, TGCTA, ATGGT, CGTTA, GTGAA, GAAAT, AGGTT, GTGTA, GACTC, ATTCG, TAATT, CATGA, TCTTA, TATTT, GCTAA, GTTTT, ATGCT, CAGTT, TACTA, AGCCA, CCCTC, CACTA, GAGGT, AACAA, TTAGG, GAGTT, CGATC, CACAG, TTTTG, TTTGA, CGGTA or GATTT, preferably, C, TCGTA, TCTTC, TTGTA, CCAAC, TGTAT, GAGTA, AGTAT, TTGTC, GTTTA, ATCGA, GTTGT, TTTTA, TGTCT, TTTAA, GTGTC, AAGGA, AAGTA, TGCTA, ATGGT, CGTTA, GTGAA, GAAAT, AGGTT, GTGTA, GACTC, ATTCG, TAATT, CATGA, GCTAA, GTTTT, ATGCT, CAGTT, TACTA, AGCCA, CCCTC, CACTA, GAGGT, GAGTT, CGATC, CACAG, TTTTG, TTTGA, CGGTA or GATTT, and more preferably, CTGAC, TCGTA, TCTTC or GAGGT.

As used herein, the term "regulatory region" refers to a nucleic acid sequence to regulate expression of nucleic acid. The regulatory region may include a sequence (homologous region) inherently liable to expression of specific nucleic acid, and may also include sequences with different origins (heterologous region) responsible for expression of different proteins and further synthetic proteins. Specifically, these sequences may be sequences of prokaryotes, eukaryotes or viral genes which promote or inhibit transcription of genes in specific or non-specific manner and inducible or non-inducible manner, or sequences derived from the same. The regulatory region may include an origin of replication, a RNA splice site, a promoter, an enhancer, a transcription terminating sequence and/or a secretion signal to induce to a secretion route of a target cell of polypeptide.

As used herein, the term "promoter" and "promoter sequence" are interchangeably used, and refer to a coding sequence or a DNA sequence able to regulate expression of functional RNA. In general, the coding sequence is positioned at 3' of the promoter sequence. The promoter is entirely derived from natural gene, consists of different components derived from different promoters discovered in nature, or may include synthetic DNA fragments. The different promoters may induce expression of genes in different tissues or cytoplasm, genes under different development steps, or genes responding to different environmental or physiological conditions. In most cases, an exact or definite boundary of the regulatory sequence is not distinguished, and therefore, it is recognized that DNA fragments with different lengths may have the same promoter activity.

Generally, a transcription initiating site is operably linked to the downstream of a promoter sequence, and extends toward the upstream (5' direction), thus to include a minimum number of base or elements required for initiating transcription in a detectable level more than the background. Within the promoter sequence, not only a protein binding domain (consensus sequence) responsible for the binding of RNA polymerase but also a transcription initiating site (for example, simply defined by a mapping process using nuclease S1) would be found.

As used herein, the term "upstream" refers to a nucleotide sequence positioned at 5' of the above mentioned nucleic acid sequence. Specifically, the upstream nucleotide sequence relates to a coding sequence or a sequence positioned at 5' of the transcription initiating site. For instance, the promoter is mostly positioned at upstream of an initiating codon. As used herein, the term "downstream" refers to a nucleotide sequence positioned at 3' of the above mentioned nucleic acid sequence.

As used herein, the term "operably linked" means association of nucleic acid sequences in a single nucleic acid fragment so that a function there of is influenced by another one. That is, this means a functional combination between a nucleic acid expression regulatory sequence (e.g., promoter, signal sequence or array at a binding position of transcription regulatory factor) and another nucleic acid sequence. Thereby, the regulatory sequence may regulate transcription and/or interpretation (or decoding) of the latter (i.e., another nucleic acid sequence). For instance, when the promoter can influence upon expression of the coding sequence (that is, the coding sequence under controlled transcription by the promoter), the promoter may be operably linked to the coding sequence. The coding sequence may be operably linked to the regulatory sequence by sense or antisense orientation.

As used herein, the term "ribosome binding site (RBS)" refers to a nucleotide sequence present on the upstream of the initiating codon in mRNA transcript to which a ribosome is bound during protein translation. This may include internal ribosome entry sites (IRES) found from mRNA of virus infecting prokaryotic or eukaryotic organisms, however, RBS generally means a bacteria sequence.

M13 bacteriophage is a virus capable of infecting *E. coli*, generally consists of thin and flexible annular tube type single-stranded DNAs surrounded by about 2700 skin proteins P8 (pVIII), has a flexible tube form, and further includes additional skin proteins p3, p6, p7 and p9. The infection is initiated as p3 receptor reaches at the terminal of F cilia. Phage proteins present in cytoplasm are p2, p10 and p5, wherein several thousands of p5 may bind to a newly synthesized single-stranded DNA to prevent formation of FR DNA. P5-DNA structure has a length of about 800 nm and a diameter of about 8 nm.

As used herein, the term "coding region" refers to a part of nucleic acid consisting of codon translated as an amino acid. "Stop codon (TAG, TGA or TAA)" may be considered as a part of the coding region even though not being translated as amino acid, however, any flanking sequence, for example, a promoter, a ribosome binding site, a transcription terminator, etc. is not regarded as a part of the coding region. Any nucleic acid or nucleic acid fragment may encode a single polypeptide or fragments, derivative or variants thereof or, otherwise, encode one or more polypeptides. For example, a single nucleic acid may encode two or more polypeptides. Further, the nucleic acid may include a regulatory element such as the promoter, the ribosome binding site or the transcription terminator, or may encode a heterologous coding region fused in a protein coding region, for example, specified element or motif such as secretive signal peptide or hetero-functional domain.

As used herein, the term "cassette", "expressing cassette" and "gene expressing cassette" refer to a DNA fragment that can be inserted into nucleic acid or polynucleotide at a specific restriction enzyme site or by homologous recombination. This DNA fragment may include polynucleotide encoding desired polypeptide, and the cassette and restriction enzyme site may be designed to ensure insertion of a cassette into an appropriate reading frame suitable for transcription and translation. A "transfection cassette" includes polynucleotide encoding the desired polypeptide, and refers to a specific vector having an element other than polynucleotide to facilitate transfection of a specific host cell. The cassette, expressing cassette, gene expressing cassette and transfection cassette may further include an element for regulating expression of polynucleotide encoding the desired polypeptide in the host. Such elements may include a promoter, an enhancer, a reaction factor, a terminator sequence, a polyadenylation sequence, etc., but it is not limited thereto.

As used herein, the term "gene" refers to polynucleotide including nucleotide that encodes a functional molecule such as a functional molecule (e.g., bioactive RNA species) to be generated only by transcription or a functional molecule (e.g., polypeptide) to be generated by transcription and translation. The term "gene" may include cDNA and genomic DNA nucleic acid. The "gene" may optionally refer to a nucleic acid fragment that includes a regulatory sequence (5'-decoding sequence) prior to an encoded region and a regulatory sequence (3'-decoding sequence) following the same, and expresses specific RNA, protein or polypeptide. The "native gene" refers to a gene having self-regulatory sequence discovered in nature. A "chimeric gene" refers to any gene other than native gene, which includes a regulatory or coding sequence not found in nature together. Therefore, the chimeric gene may include regulatory and coding sequences derived from other sources or, otherwise, regulatory and coding sequences that are arranged in different manners from those found in nature, even though being derived from the same source. An "endogenous gene" refers to a native gene present in the original site within a genome of an organism. A "foreign" gene or "heterologous" gene refers to a gene generally not found in a host organism, but transferred to the host organism by gene delivery. The foreign gene may include the native gene inserted into non-native organism or the chimeric gene. A "transgene" or "transfer gene" is a gene introduced into a cell during gene delivery.

As used herein, the term "mutation" may mean substitution, deletion, addition or replacement of one or a plurality of nucleic acids.

As used herein, the term "expression" refers to biological production of a product encoded by a coding sequence. In most cases, DNA sequence including the coding sequence is under transcription to form a messenger-RNA (mRNA). Then, the messenger-RNA is translated to form a polypeptide product having biological activity associated with the same. Further, the expression process may include additional processing of the RNA transcription product (for example, splicing to remove intron) and/or post-translation processing of the polypeptide product.

As used herein, the term "host cell" may include prokaryote (e.g., bacteria) and eukaryote (e.g., fungi, yeast, animal, insect, plant), and may be any desirable cell for DNA production. It is preferable to be a cell having F cilia. Appropriate prokaryotic host cell may be *E. coli* having F cilia, and may include DH5α, XL1blue or Jude1 DH10B, but it is not limited thereto.

As used herein, the term "primer" refers to oligonucleotide which is hybridized with a target nucleic acid to form a double-stranded nucleic acid region that can act as an initiating point for DNA synthesis under desirable conditions. Such primers may be used in polymerase chain reaction or for DNA sequence analysis.

Hereinafter, a method of the present invention will be described in detail.

In M13 p5 expressing cassette including a promoter, a ribosome binding site (RBS) and a protein 5 (p5) coding region in M13 bacteriophage, at least one base, at least two continuous or non-continuous bases, at least three continuous or non-continuous bases, at least four continuous or non-continuous bases or five bases among the sequence between the RBS and the p5 coding region are under mutation, a host cell is infected with the mutated M13 bacteriophage, followed by culturing the host cell, thereby increasing DNA production.

The culturing may be performed using an appropriate culture medium under suitable culture conditions well known in the related art. The culture medium and culture conditions may be altered by those skilled in the art. For instance, the culture medium may be a liquid medium, but it is not limited thereto. The culturing method may include, for example, batch culture, continuous culture, fed-batch culture or a combination thereof, but it is not limited thereto.

The culture medium needs suitable conditions for specific strains, which may be desirably altered by those skilled in the art. The culture medium may include diverse carbon sources, nitrogen sources and trace elements. The carbon source possibly used in the culture medium may include, but it is not limited to: e.g., sugar or carbohydrate such as glucose, sucrose, lactose, fructose, maltose, starch and cellulose; e.g., oil and fat such as soybean oil, sunflower oil, castor oil, coconut oil, etc.; e.g., fatty acid such as palmitic acid, stearic acid and linoleic acid; alcohol such as glycol and ethanol; and organic acid such as acetic acid, which may be used alone or in combination of two or more thereof. The nitrogen source possibly used in the culture medium may include, but it is not limited to: e.g., organic substances such as peptone, yeast extract, meat extract, molt extract, corn steep liquor, beans powder and urea; and non-organic substances such as ammonium sulfate, ammonium chloride, ammonium phosphate, ammonium carbonate and ammonium nitrate, which may be used alone or in combination of two or more thereof. A potassium source possibly used in the culture medium may include, but it is not limited to, potassium dihydrogen phosphate, dipotassium hydrogen phosphate, and sodium-containing salts corresponding to the same. According to some embodiments, the culture medium may include a metal salt necessary to growth such as magnesium sulfate or iron sulfate, etc., but it is not limited thereto. According to some embodiments, in addition to the above components, essential amino acids and vitamins may be further included. According to some embodiments, the culture medium may further include an appropriate precursor. The culture medium or individual components may be added to a culture solution in any suitable manner, for example, in a batch or continuous manner, but it is not limited thereto.

In some embodiments, pH of the culture may be properly adjusted to match to a selected microorganism by adding a compound such as ammonium hydroxide, potassium hydroxide, ammonia, phosphoric acid or sulfuric acid to the culture in a suitable manner during incubation. In some embodiments, a defoaming agent such as fatty acid polyglycol ester may be used to inhibit foaming in the culture during incubation. In order to maintain the culture in an aerobic condition, oxygen or oxygen-containing gas (e.g., air) may be fed to the culture. For instance, a temperature of the culture may be maintained in a range of about 20 to 45° C. Further, in some embodiments, the temperature may be maintained in a range of about 25 to 40° C. For instance, the incubation may be conducted for about 8 to 160 hours, for example, until it reaches a desired amount of DNA.

Hereinafter, the present invention will be concretely described by following examples.

Example 1. p5 Expressing Cassette Mutant and Expectation of Expression Level by the Same p5 expressing cassette includes a promoter, a RBS and p5 coding sequence, wherein there are several base sequences between the RBS and the p5 coding sequence. In the present invention, such several sequences are named as a spacer.

The present inventors have introduced M13mp18 vector purchased from New England Biolabs into *E. coli* XL1blue by heat shocking to produce double-stranded DNAs (dsDNA) and purified the same by Exprep™ Plasmid SV (GeneAll, Korea). Then, a kanamycin resistant gene KanR as a molecule marker was introduced into the produced dsDNA, which was named as M13mp18k (SEQ ID NO. 18).

Using UTR designer (https://sbi.postech.ac.kr/utr designer/), a promoter region and a ribosome binding site (RBS) were confirmed, thereby identifying the spacer sequence between the RBS sequence and the p5 coding region. Therefore, DNA sequence of a native p5 expressing cassette including the promoter, RBS, spacer and p5 coding region was represented by SEQ ID No. 1.

In order to randomly mutate the spacer sequence, M13mp18k vector was divided into two fragments, and then, the first fragment and the second fragment were subjected to PCR at annealing temperatures of 58 and 59° C., respectively, wherein PCR for the first fragment was conducted using M13mp18pV TCACA random mut. 1F (ttaaaatcgcataaggtaatNNNNNATGATTAAAGTTGAAAT-TAAACCATC, SEQ ID NO. 14) and M13mp18pV TCACA random mut. 1R (attttgacgcTCAATCGTCTGAAATGGAT-TATTTAC, SEQ ID NO. 15) as primers, while PCR for the second fragment was conducted using M13mp18pV TCACA random mut. 2F (agacgattgaGCGT-CAAAATGTAGGTATTTC, SEQ ID NO. 16) and M13mp18pV TCACA random mut. 2R (ATTACCTTATGC-GATTTTAAGAAC, SEQ ID NO. 17) as primers, followed by conjugating both of these fragments, thereby preparing 71 types of mutant candidates (18k-1 to 18k-71, see FIG. 11) that may decrease p5 protein expression.

Each of the prepared mutants was introduced into *E. coli* XL1blue strain and inoculated on 5 ml of LB medium in a 15 ml conical tube for incubation. Production of M13 phage was measured and illustrated as a ratio of production to that of a product obtained by culturing native M13 under the same conditions (FIG. 1).

Among those mutants, with regard to the mutant having a relative phage production of 1 or more compared to the native M13, the phage was produced on 25 ml M9 2× medium in a 250 ml flask and a relative phage production to the native M13 was determined. 18k-5, 18k-7, 18k-10 and 18k-62 mutants showing consistent results were selected.

TABLE 1

| Phage | Spacer sequence |
|---|---|
| 18k-0 (WT) (SEQ ID NO. 1) | TCACA (SEQ ID NO. 5) |
| 18k-5 (SEQ ID NO. 10) | CTGAC (SEQ ID NO. 6) |
| 18k-7 (SEQ ID NO. 11) | TCGTA (SEQ ID NO. 7) |
| 18k-10 (SEQ ID NO. 12) | TCTTC (SEQ ID NO. 8) |
| 18k-62 (SEQ ID NO. 13) | GAGGT (SEQ ID NO. 9) |

By inputting promoter-RBS-spacer-p5 coding sequences of the selected mutants in UTR designer (https://sbi.postech.ac.kr/utr designer/), RBS binding intensity was estimated whereby an expression level of p5 protein was expected from the estimated results (Table 2).

TABLE 2

| Spacer sequence | Estimated p5 expression level |
|---|---|
| 18k-0 | 314958.9 |
| 18k-5 | 102908.7 |
| 18k-7 | 453043.1 |
| 18k-10 | 251821.9 |
| 18k-62 | 87012.5 |

Example 2. Measurement of Single-Stranded DNA Production 18k-5, 18k-7, 18k-10 and 18k-62 phages obtained in Example 1, which were expected to reduce p5 expression level, were used to infect a host cell expressing F cilia, that is, XL1blue endA1 gyrA96 (nal$^R$) thi-1 recA1 relA1 lac glnV44 F' [::Tn10 proAB$^+$lacI$^q$Δ(lacZ)M15] hsdR17 ($r_K^-$ $m_X^+$) strain, followed by incubation in 25 ml of culture medium (2XM9 (Na$_2$HPO$_4$ 12 g/L, KH$_2$PO$_4$ 6 g/L, NaCl 1 g/L, NH$_4$Cl 2 g/L)+citrate 1.7 g/L+thiamine 25 mg/L) for 27 hours. Herein, the native phage 18k-0 was used as a control group. The phage was collected by PEG precipitation, and after measuring an absorbance at 230 to 400 nm, a concentration was determined by the following equation.

$$(A269-A320) \times (6 \times 10^{16})/\text{number of bases/virion} = \text{PFU/ml}$$

The measured results were indicated as a ratio of phage production when each phage mutant was inoculated to phage production when 18k-0 was inoculated (Table 3, FIG. 2).

TABLE 3

| Phage | Relative production of phage |
|---|---|
| 18k-0 (WT) | 1 |
| 18k-5 | 2.432817 |
| 18k-7 | 2.376569 |
| 18k-10 | 2.270974 |
| 18k-62 | 2.129119 |

Further, a concentration of single-stranded DNAs was determined by the following equation after measuring absorbance at 260 nm using a nano-spectrometer.

$$A260*33 = \text{ssDNA concentration (ng/ul)}$$

The determined results are shown in Table 4 below and FIG. 3.

TABLE 4

| Phage | ssDNA concentration (260/280) | Relative ssDNA production |
|---|---|---|
| 18k-0 (WT) | 380 | 1 |
| 18k-5 | 1330 | 3.5 |
| 18k-7 | 790 | 2.07895 |
| 18k-10 | 920 | 2.42105 |
| 18k-62 | 1138 | 2.99474 |

Example 3. Measurement of p5 Production

The 18k-0, 18k-5, 18k-7, 18k-10 and 18k-62 phages, respectively, were used to infect a host cell expressing F cilia, that is, Jude1 DH10B F' [proAB lacI$^Q$ lacZ ΔM15 Tn10(Tet$^R$)] strain, followed by incubation in 25 ml of culture medium (2XM9 (Na$_2$HPO$_4$ 12 g/L, KH$_2$PO$_4$ 6 g/L, NaCl 1 g/L, NH$_4$Cl 2 g/L)+citrate 1.7 g/L+thiamine 25 mg/L+leucine 40 mg/L) for 27 hours. The native phage 18k-0 was used as a control group. Production of the phage was measured in the same manner as described in Example 2, and the measured results were indicated as a relative amount to 18k-0 (Table 5, FIG. 4).

TABLE 5

| Phage | Relative production of phage |
|---|---|
| 18k-0 | 1 |
| 18k-5 | 1.114822 |
| 18k-7 | 1.212842 |
| 18k-10 | 1.207001 |
| 18k-62 | 1.36875 |

[Sequence Listing]

| Sequence number | Description |
|---|---|
| 1 | Native p5 protein expressing cassette sequence |
| 2 | Promoter sequence of native p5 protein expressing cassette |
| 3 | RBS sequence of native p5 protein expressing cassette |
| 4 | p5 coding region sequence of native p5 protein expressing cassette |
| 5 | Spacer sequence of 18k-0 |
| 6 | Spacer sequence of 18k-5 |

-continued

[Sequence Listing]

| Sequence number | Description |
|---|---|
| 7 | Spacer sequence of 18k-7 |
| 8 | Spacer sequence of 18k-10 |
| 9 | Spacer sequence of 18k-62 |
| 10 | p5 protein expressing cassette sequence of 18-5 |
| 11 | p5 protein expressing cassette sequence of 18k-7 |
| 12 | p5 protein expressing cassette sequence of 18k-10 |
| 13 | p5 protein expressing cassette sequence of 18k-62 |
| 14 | M13mp18pV TCACA random mut. 1F sequence |
| 15 | M13mp18pV TCACA random mut. 1R sequence |
| 16 | M13mp18pV TCACA random mut. 2F sequence |
| 17 | M13mp18pV TCACA random mut. 2R sequence |
| 18 | M13mp18k full length sequence |

For the purpose of establishing claims, the appended claims should not be interpreted in a narrow range more than the meanings of a terminology itself used therein, whereby illustrative embodiments in the specification should not be directly considered as the claims. Accordingly, it should be understood that the present invention has been described by means of illustrative embodiments, which substantially do not limit the claims. Therefore, the scope of the present invention is only restricted by the appended claims. All published documents, patents, patent applications and journal articles are introduced herein, the entire contents of which are incorporated by reference.

What is claimed is:

1. A gene comprising:
   an M13 p5 expressing cassette which includes a promoter, a ribosome binding site (RBS) and a protein 5 (p5) coding region,
   wherein the sequence between the RBS and the p5 coding region is selected from the group consisting of SEQ ID NO. 6, SEQ ID NO. 7, SEQ ID NO. 8, and SEQ ID NO. 9.

2. The gene according to claim 1, wherein the RBS sequence is represented by SEQ ID NO. 3, and the p5 coding region is represented by SEQ ID NO. 4.

3. The gene according to claim 1, wherein the p5 expressing cassette includes a sequence represented by any one sequence selected from the group consisting of SEQ ID NO. 10, SEQ ID NO. 11, SEQ ID NO. 12, and SEQ ID NO. 13.

4. An M13 bacteriophage comprising the gene according to claim 1.

5. A host cell comprising the gene according to claim 1.

6. A host cell infected with the M13 bacteriophage according to claim 4.

7. The host cell according to claim 5, wherein the host cell expresses F cilia.

8. The host cell according to claim 6, wherein the host cell expresses F cilia.

9. A method for increasing production of DNA, comprising:
   mutating sequences between a ribosome binding site (RBS) and a protein 5 (p5) coding region into any one sequence selected from the group consisting of SEQ ID NO. 6, SEQ ID NO. 7, SEQ ID NO. 8, and SEQ ID NO. 9 in an M13 p5 expressing cassette which includes a promoter in M13 bacteriophage, the RBS and the p5 coding region; and
   infecting a host cell with the mutant M13 bacteriophage.

10. The method according to claim 9, wherein the RBS sequence is represented by SEQ ID NO. 3, and the p5 coding region is represented by SEQ ID NO. 4.

11. The method according to claim 9, wherein the p5 expressing cassette includes a sequence represented by any one sequence selected from the group consisting of SEQ ID NO. 10, SEQ ID NO. 11, SEQ ID NO. 12, and SEQ ID NO. 13.

12. The method according to claim 9, wherein the host cell expresses F cilia.

\* \* \* \* \*

SEQUENCE LISTING

```
<160> NUMBER OF SEQ ID NOS: 18

<210> SEQ ID NO 1
<211> LENGTH: 339
<212> TYPE: DNA
<213> ORGANISM: Artificial Sequence
<220> FEATURE:
<223> OTHER INFORMATION: M13mp18k
<220> FEATURE:
<221> NAME/KEY: gene
<222> LOCATION: (1)..(339)
<223> OTHER INFORMATION: wild type p5-expressing cassette

<400> SEQUENCE: 1
taacgtagat ttttcttccc aacgtcctga ctggtataat gagccagttc ttaaaatcgc      60
ataaggtaat tcacaatgat taaagttgaa attaaaccat ctcaagccca atttactact     120
cgttctggtg tttctcgtca gggcaagcct tattcactga atgagcagct ttgttacgtt     180
gatttgggta atgaatatcc ggttcttgtc aagattactc ttgatgaagg tcagccagcc     240
tatgcgcctg gtctgtacac cgttcatctg tcctctttca aagttggtca gttcggttcc     300
cttatgattg accgtctgcg cctcgttccg gctaagtaa                             339

<210> SEQ ID NO 2
<211> LENGTH: 50
<212> TYPE: DNA
<213> ORGANISM: Artificial Sequence
<220> FEATURE:
<223> OTHER INFORMATION: M13mp18k
<220> FEATURE:
<221> NAME/KEY: promoter
<222> LOCATION: (1)..(50)
<223> OTHER INFORMATION: promoter of wild type p5-expressing cassette

<400> SEQUENCE: 2
```

```
taacgtagat ttttcttccc aacgtcctga ctggtataat gagccagttc        50
```

<210> SEQ ID NO 3
<211> LENGTH: 6
<212> TYPE: DNA
<213> ORGANISM: Artificial Sequence
<220> FEATURE:
<223> OTHER INFORMATION: M13mp18k
<220> FEATURE:
<221> NAME/KEY: RBS
<222> LOCATION: (1)..(6)
<223> OTHER INFORMATION: RBS of wild type p5-expressing cassette

<400> SEQUENCE: 3

```
ggtaat                                                        6
```

<210> SEQ ID NO 4
<211> LENGTH: 264
<212> TYPE: DNA
<213> ORGANISM: Artificial Sequence
<220> FEATURE:
<223> OTHER INFORMATION: M13mp18k
<220> FEATURE:
<221> NAME/KEY: gene
<222> LOCATION: (1)..(264)
<223> OTHER INFORMATION: p5 coding sequence

<400> SEQUENCE: 4

```
atgattaaag ttgaaattaa accatctcaa gcccaattta ctactcgttc tggtgtttct   60
cgtcagggca agccttattc actgaatgag cagctttgtt acgttgattt gggtaatgaa  120
tatccggttc ttgtcaagat tactcttgat gaaggtcagc cagccatgc gcctggtctg  180 tacaccgttc atctgtcctc tttcaaagtt ggtcagttcg gttcccttat gattgaccgt  240
ctgcgcctcg ttccggctaa gtaa                                        264
```

<210> SEQ ID NO 5
<211> LENGTH: 5
<212> TYPE: DNA
<213> ORGANISM: Artificial Sequence
<220> FEATURE:
<223> OTHER INFORMATION: M13mp18k
<220> FEATURE:
<221> NAME/KEY: gene
<222> LOCATION: (1)..(5)
<223> OTHER INFORMATION: spacer sequence of 18k-0 p5-expressing cassette

<400> SEQUENCE: 5

```
tcaca                                                         5
```

<210> SEQ ID NO 6
<211> LENGTH: 5
<212> TYPE: DNA
<213> ORGANISM: Artificial Sequence
<220> FEATURE:
<223> OTHER INFORMATION: M13mp18k
<220> FEATURE:
<221> NAME/KEY: gene
<222> LOCATION: (1)..(5)
<223> OTHER INFORMATION: spacer sequence of 18k-5 p5-expressing cassette

<400> SEQUENCE: 6

```
ctgac                                                         5
```

<210> SEQ ID NO 7
<211> LENGTH: 5
<212> TYPE: DNA
<213> ORGANISM: Artificial Sequence

```
<220> FEATURE:
<223> OTHER INFORMATION: M13mp18k
<220> FEATURE:
<221> NAME/KEY: gene
<222> LOCATION: (1)..(5)
<223> OTHER INFORMATION: spacer sequence of 18k-7 p5-expressing cassette

<400> SEQUENCE: 7 tcgta                                                                     5

<210> SEQ ID NO 8
<211> LENGTH: 5
<212> TYPE: DNA
<213> ORGANISM: Artificial Sequence
<220> FEATURE:
<223> OTHER INFORMATION: M13mp18k
<220> FEATURE:
<221> NAME/KEY: gene
<222> LOCATION: (1)..(5)
<223> OTHER INFORMATION: spacer sequence of 18k-10 p5-expressing
      cassette

<400> SEQUENCE: 8 tcttc                                                                     5

<210> SEQ ID NO 9
<211> LENGTH: 5
<212> TYPE: DNA
<213> ORGANISM: Artificial Sequence
<220> FEATURE:
<223> OTHER INFORMATION: M13mp18k
<220> FEATURE:
<221> NAME/KEY: gene
<222> LOCATION: (1)..(5)
<223> OTHER INFORMATION: spacer sequence of 18k-62 p5-expressing
      cassette

<400> SEQUENCE: 9 gaggt                                                                     5

<210> SEQ ID NO 10
<211> LENGTH: 339
<212> TYPE: DNA
<213> ORGANISM: Artificial Sequence
<220> FEATURE:
<223> OTHER INFORMATION: M13mp18k
<220> FEATURE:
<221> NAME/KEY: gene
<222> LOCATION: (1)..(339)
<223> OTHER INFORMATION: 18k-5 p5-expressing cassette

<400> SEQUENCE: 10
taacgtagat ttttcttccc aacgtcctga ctggtataat gagccagttc ttaaaatcgc        60
ataaggtaat ctgacatgat taaagttgaa attaaaccat ctcaagccca atttactact       120
cgttctggtg tttctcgtca gggcaagcct tattcactga atgagcagct tgttacgtt        180 gatttgggta atgaatatcc ggttcttgtc aagattactc ttgatgaagg tcagccagcc       240
tatgcgcctg gtctgtacac cgttcatctg tcctctttca aagttggtca gttcggttcc       300
cttatgattg accgtctgcg cctcgttccg gctaagtaa                              339

<210> SEQ ID NO 11
<211> LENGTH: 339
<212> TYPE: DNA
<213> ORGANISM: Artificial Sequence
<220> FEATURE:
<223> OTHER INFORMATION: M13mp18k
<220> FEATURE:
```

```
<221> NAME/KEY: gene
<222> LOCATION: (1)..(339)
<223> OTHER INFORMATION: 18k-7 p5-expressing cassette

<400> SEQUENCE: 11
taacgtagat ttttcttccc aacgtcctga ctggtataat gagccagttc ttaaaatcgc    60
ataaggtaat tcgtaatgat taaagttgaa attaaaccat ctcaagccca atttactact   120
cgttctggtg tttctcgtca gggcaagcct tattcactga atgagcagct ttgttacgtt   180
gatttgggta atgaatatcc ggttcttgtc aagattactc ttgatgaagg tcagccagcc   240
tatgcgcctg gtctgtacac cgttcatctg tcctctttca aagttggtca gttcggttcc   300
cttatgattg accgtctgcg cctcgttccg gctaagtaa                          339

<210> SEQ ID NO 12
<211> LENGTH: 339
<212> TYPE: DNA
<213> ORGANISM: Artificial Sequence
<220> FEATURE:
<223> OTHER INFORMATION: M13mp18k
<220> FEATURE:
<221> NAME/KEY: gene
<222> LOCATION: (1)..(339)
<223> OTHER INFORMATION: 18k-10 p5-expressing cassette

<400> SEQUENCE: 12
taacgtagat ttttcttccc aacgtcctga ctggtataat gagccagttc ttaaaatcgc    60
ataaggtaat tcttcatgat taaagttgaa attaaaccat ctcaagccca atttactact   120
cgttctggtg tttctcgtca gggcaagcct tattcactga atgagcagct ttgttacgtt   180
gatttgggta atgaatatcc ggttcttgtc aagattactc ttgatgaagg tcagccagcc   240
tatgcgcctg gtctgtacac cgttcatctg tcctctttca aagttggtca gttcggttcc   300
cttatgattg accgtctgcg cctcgttccg gctaagtaa                          339

<210> SEQ ID NO 13
<211> LENGTH: 339
<212> TYPE: DNA
<213> ORGANISM: Artificial Sequence
<220> FEATURE:
<223> OTHER INFORMATION: M13mp18k
<220> FEATURE:
<221> NAME/KEY: gene
<222> LOCATION: (1)..(339)
<223> OTHER INFORMATION: 18k-62 p5-expressing cassette

<400> SEQUENCE: 13
taacgtagat ttttcttccc aacgtcctga ctggtataat gagccagttc ttaaaatcgc    60
ataaggtaat gaggtatgat taaagttgaa attaaaccat ctcaagccca atttactact   120
cgttctggtg tttctcgtca gggcaagcct tattcactga atgagcagct ttgttacgtt   180
gatttgggta atgaatatcc ggttcttgtc aagattactc ttgatgaagg tcagccagcc   240
tatgcgcctg gtctgtacac cgttcatctg tcctctttca aagttggtca gttcggttcc   300
cttatgattg accgtctgcg cctcgttccg gctaagtaa                          339

<210> SEQ ID NO 14
<211> LENGTH: 51
<212> TYPE: DNA
<213> ORGANISM: Artificial Sequence
<220> FEATURE:
<223> OTHER INFORMATION: M13mp18pV TCACA random mut. 1F primer
<220> FEATURE:
<221> NAME/KEY: misc_feature
```

<222> LOCATION: (21)..(25)
<223> OTHER INFORMATION: n is a, c, g, or t

<400> SEQUENCE: 14
ttaaaatcgc ataaggtaat nnnnnatgat taaagttgaa attaaaccat c         51

<210> SEQ ID NO 15
<211> LENGTH: 36
<212> TYPE: DNA
<213> ORGANISM: Artificial Sequence
<220> FEATURE:
<223> OTHER INFORMATION: M13mp18pV TCACA random mut. 1R primer

<400> SEQUENCE: 15
attttgacgc tcaatcgtct gaaatggatt atttac                          36

<210> SEQ ID NO 16
<211> LENGTH: 31
<212> TYPE: DNA
<213> ORGANISM: Artificial Sequence
<220> FEATURE:
<223> OTHER INFORMATION: M13mp18pV TCACA random mut. 2F primer

<400> SEQUENCE: 16
agacgattga gcgtcaaaat gtaggtattt c                               31

<210> SEQ ID NO 17
<211> LENGTH: 24
<212> TYPE: DNA
<213> ORGANISM: Artificial Sequence
<220> FEATURE:
<223> OTHER INFORMATION: M13mp18pV TCACA random mut. 2R primer

<400> SEQUENCE: 17
attaccttat gcgattttaa gaac                                       24

<210> SEQ ID NO 18
<211> LENGTH: 8582
<212> TYPE: DNA
<213> ORGANISM: Artificial Sequence
<220> FEATURE:
<223> OTHER INFORMATION: M13mp18k full sequence

<400> SEQUENCE: 18
gtacccgggg atcctctaga gtcgacctgc aggcatgcaa gcttggcact ggccgtcgtt    60
ttacaacgtc gtgactggga aaaccctggc gttacccaac ttaatcgcct tgcagcacat   120
ccccctttcg ccagctggcg taatagcgaa gaggcccgca ccgatcgccc ttcccaacag   180
ttgcgcagcc tgaatggcga atggcgcttt gcctggtttc cggcaccaga agcggtgccg   240
gaaagctggc tggagtgcga tcttcctgag gccgatactg tcgtcgtccc ctcaaactgg   300
cagatgcacg gttacgatgc gcccatctac accaacgtga cctatcccat tacggtcaat   360
ccgccgtttg ttcccacgga gaatccgacg ggttgttact cgctcacatt taatgttgat   420
gaaagctggc tacaggaagg ccagacgcga attatttttg atggcgttcc tattggttaa   480
aaaatgagct gatttaacaa aaatttaatg cgaattttaa caaaatatta acgtttacaa   540
tttaaatatt tgcttataca atcttcctgt ttttggggct tttctgatta tcaaccgggg   600
tacatatgat tgacatgcta gttttacgat taccgttcat cgattctctt gtttgctcca   660
gactctcagg caatgacctg atagcctttg tagatctctc aaaaatagct accctctccg   720
gcattaattt atcagctaga acggttgaat atcatattga tggtgatttg actgtctccg   780

-continued

```
gcctttctca ccctttttgaa tctttaccta cacattactc aggcattgca tttaaaatat    840
atgagggttc taaaaatttt tatccttgcg ttgaaataaa ggcttctccc gcaaaagtat    900
tacagggtca taatgttttt ggtacaaccg atttagcttt atgctctgag ctttattgc    960
ttaattttgc taattctttg ccttgcctgt atgattatt ggatgttaat gctactacta   1020
ttagtagaat tgatgccacc ttttcagctc gcgccccaaa tgaaaatata gctaaacagg   1080
ttattgacca tttgcgaaat gtatctaatg gtcaaactaa atctactcgt tcgcagaatt   1140
gggaatcaac tgttatatgg aatgaaactt ccagacaccg tactttagtt gcatatttaa   1200
aacatgttga gctacagcat tatattcagc aattaagctc taagccatcc gcaaaaatga   1260
cctcttatca aaaggagcaa ttaaaggtac tctctaatcc tgacctgttg gagtttgctt   1320
ccggtctggt tcgctttgaa gctcgaatta aaacgcgata tttgaagtct ttcgggcttc   1380
ctcttaatct ttttgatgca atccgctttg cttctgacta atagtcag ggtaaagacc   1440
tgattttga tttatggtca ttctcgtttt ctgaactgtt taaagcattt gagggggatt   1500
caatgaatat ttatgacgat tccgcagtat tggacgctat ccagtctaaa cattttacta   1560
ttacccctc tggcaaaact tcttttgcaa aagcctctcg ctattttggt ttttatcgtc   1620
gtctggtaaa cgagggttat gatagtgttg ctcttactat gcctcgtaat tccttttggc   1680
gttatgtatc tgcattagtt gaatgtggta ttcctaaatc tcaactgatg aatctttcta   1740
cctgtaataa tgttgttccg ttagttcgtt ttattaacgt agattttct tcccaacgtc   1800
ctgactggta taatgagcca gttcttaaaa tcgcataagg taattcacaa tgattaaagt   1860
tgaaattaaa ccatctcaag cccaatttac tactcgttct ggtgtttctc gtcagggcaa   1920
gccttattca ctgaatgagc agctttgtta cgttgatttg ggtaatgaat atccggttct   1980
tgtcaagatt actcttgatg aaggtcagcc agcctatgcg cctggtctgt acaccgttca   2040
tctgtcctct ttcaaagttg gtcagttcgg ttcccttatg attgaccgtc tgcgcctcgt   2100
tccggctaag taacatggag caggtcgcgg atttcgacac aatttatcag gcgatgatac   2160
aaatctccgt tgtactttgt ttcgcgcttg gtataatcgc tgggggtcaa agatgagtgt   2220
tttagtgtat tcttttgcct cttttcgtttt aggttggtgc cttcgtagtg cattacgta   2280
ttttacccgt ttaatggaaa cttcctcatg aaaaagtctt tagtcctcaa agcctctgta   2340
gccgttgcta ccctcgttcc gatgctgtct ttcgctgctg agggtgacga tcccgcaaaa   2400
gcggccttta actccctgca agcctcagcg accgaatata tcggttatgc gtgggcgatg   2460
gttgttgtca ttgtcggcgc aactatcggt atcaagctgt ttaagaaatt cacctcgaaa   2520
gcaagctgat aaaccgatac aattaaaggc tccttttgga ccttttttt tggagatttt   2580
caacgtgaaa aaattattat tcgcaattcc tttagttgtt cctttctatt ctcactccgc   2640
tgaaactgtt gaaagttgtt tagcaaaatc ccatacagaa aattcattta ctaacgtctg   2700
gaaagacgac aaaactttag atcgttacgc taactatgag ggctgtctgt ggaatgctac   2760
aggcgttgta gtttgtactg gtgacgaaac tcagtgttac ggtacatggg ttcctattgg   2820
gcttgctatc cctgaaaatg agggtggtgg ctctgagggt ggcggttctg agggtggcgg   2880
ttctgagggt ggcggtacta aacctcctga gtacggtgat acacctattc cgggctatac   2940
ttatatcaac cctctcgacg gcacttatcc gcctggtact gagcaaaacc ccgctaatcc   3000
taatccttct cttgaggagt ctcagcctct taatactttc atgtttcaga ataataggtt   3060
ccgaaatagg caggggggcat taactgttta tacgggcact gttactcaag cactgacccc   3120
cgttaaaaact tattaccagt acactcctgt atcatcaaaa gccatgtatg acgcttactg   3180
```

```
gaacggtaaa ttcagagact gcgctttcca ttctggcttt aatgaggatt tatttgtttg    3240
tgaatatcaa ggccaatcgt ctgacctgcc tcaacctcct gtcaatgctg gcggcggctc    3300
tggtggtggt tctggtggcg gctctgaggg tggtggctct gagggtggcg gttctgaggg    3360
tggcggctct gagggaggcg gttccggtgg tggctctggt tccggtgatt ttgattatga    3420
aaagatggca aacgctaata agggggctat gaccgaaaat gccgatgaaa acgcgctaca    3480
gtctgacgct aaaggcaaac ttgattctgt cgctactgat tacggtgctg ctatcgatgg    3540
tttcattggt gacgtttccg gccttgctaa tggtaatggt gctactggtg attttgctgg    3600
ctctaattcc caaatggctc aagtcggtga cggtgataat tcacctttaa tgaataattt    3660
ccgtcaatat ttaccttccc tccctcaatc ggttgaatgt cgcccttttg tctttggcgc    3720
tggtaaacca tgaattttt ctattgattg tgacaaaata aacttattcc gtggtgtctt    3780
tgcgtttctt ttatatgttg ccaccttat gtatgtattt tctacgtttg ctaacatact    3840
gcgtaataag gagtcttaat catgccagtt cttttgggta ttccgttatt attgcgtttc    3900
ctcggtttcc ttctggtaac tttgttcggc tatctgctta cttttcttaa aagggcttc    3960 ggtaagatag ctattgctat ttcattgttt cttgctctta ttattgggct taactcaatt    4020
cttgtgggtt atctctctga tattagcgct caattaccct ctgactttgt tcagggtgtt    4080
cagttaattc tcccgtctaa tgcgcttccc tgttttatg ttattctctc tgtaaaggct    4140 gctatttca tttttgacgt taaacaaaaa atcgtttctt atttggattg ggataaataa    4200
tatggctgtt tattttgtaa ctggcaaatt aggctctgga aagacgctcg ttagcgttgg    4260
taagattcag gataaaattg tagctgggtg caaaatagca actaatcttg atttaaggct    4320
tcaaaacctc ccgcaagtcg ggaggttcgc taaaacgcct cgcgttctta gaataccgga    4380 taagcctttct atatctgatt tgcttgctat tgggcgcggt aatgattcct acgatgaaaa    4440
taaaaacggc ttgcttgttc tcgatgagtg cggtacttgg tttaataccc gttcttggaa    4500
tgataaggaa agacagccga ttattgattg gtttctacat gctcgtaaat taggatggga    4560
tattattttt cttgttcagg acttatctat tgttgataaa caggcgcgtt ctgcattagc    4620
tgaacatgtt gtttattgtc gtcgtctgga cagaattact ttacctttg tcggtacttt    4680 atattctctt attactggct cgaaaatgcc tctgcctaaa ttacatgttg gcgttgttaa    4740
atatggcgat tctcaattaa gccctactgt tgagcgttgg ctttatactg gtaagaattt    4800
gtataacgca tatgatacta aacaggcttt ttctagtaat tatgattccg gtgtttattc    4860
ttatttaacg ccttatttat cacacggtcg gtatttcaaa ccattaaatt taggtcagaa    4920
gatgaaatta actaaaatat atttgaaaaa gttttctcgc gttctttgtc ttgcgattgg    4980
atttgcatca gcatttacat atagttatat aacccaacct aagccggagg ttaaaaaggt    5040
agtctctcag acctatgatt ttgataaatt cactattgac tcttctcagc gtcttaatct    5100
aagctatcgc tatgttttca aggattctaa gggaaaatta attaatagcg acgatttaca    5160
gaagcaaggt tattcactca catatattga tttatgtact gtttccatta aaaaaggtaa    5220
ttcaaatgaa attgttaaat gtaattaatt ttgttttctt gatgtttgtt tcatcatctt    5280
cttttgctca ggtaattgaa atgaataatt cgcctctgcg cgattttgta acttggtatt    5340
caaagcaatc aggcgaatcc gttattgttt ctcccgatgt aaaaggtact gttactgtat    5400
attcatctga cgttaaacct gaaaatctac gcaattctt tatttctgtt ttacgtgcaa    5460
ataattttga tatggtaggt tctaaccctt ccattattca gaagtataat ccaaacaatc    5520
```

```
aggattatat tgatgaattg ccatcatctg ataatcagga atatgatgat aattccgctc   5580
cttctggtgg tttctttgtt ccgcaaaatg ataatgttac tcaaacttt  aaaattaata   5640 acgttcgggc aaaggattta atacgagttg tcgaattgtt tgtaaagtct aatacttcta   5700
aatcctcaaa tgtattatct attgacggct ctaatctatt agttgttagt gctcctaaag   5760
atattttaga taaccttcct caattccttt caactgttga tttgccaact gaccagatat   5820
tgattgaggg tttgatattt gaggttcagc aaggtgatgc tttagatttt tcatttgctg   5880
ctggctctca gcgtggcact gttgcaggcg tgttaatac  tgaccgcctc acctctgttt   5940
tatcttctgc tggtggttcg ttcggtattt taatggcga  tgttttaggg ctatcagttc   6000
gcgcattaaa gactaatagc cattcaaaaa tattgtctgt gccacgtatt cttacgcttt   6060
caggtcagaa gggttctatc tctgttggcc agaatgtccc ttttattact ggtcgtgtga   6120
ctggtgaatc tgccaatgta ataatccat  ttcagacgat tgagcgtcaa aatgtaggta   6180
tttccatgag cgttttcct  gttgcaatgg ctggcggtaa tattgttctg gatattacca   6240
gcaaggccga tagtttgagt tcttctactc aggcaagtga tgttattact aatcaaagaa   6300
gtattgctac aacggttaat ttgcgtgatg gacagactct tttactcggt ggcctcactg   6360
attataaaaa cacttctcag gattctggcg taccgttcct gtctaaaatc cctttaatcg   6420
gcctcctgtt tagctcccgc tctgattcta acgaggaaag cacgttatac gtgctcgtca   6480
aagcaaccat agtacgcgcc ctgtagcggc gcattaagcg cggcgggtgt ggtggttacg   6540
cgcagcgtga ccgctacact tgccagcgcc ctagcgcccg ctcctttcgc tttcttccct   6600
tcctttctcg ccacgttcgc cggctttccc cgtcaagctc taaatcgggg gctcccttta   6660
gggttccgat ttagtgcttt acggcacctc gaccccaaaa aacttgattt gggtgatggt   6720
tcacgtagtg ggccatcgcc ctgatagacg gttttcgcc  ctttgacgtt ggagtccacg   6780
ttctttaata gtggactctt gttccaaact ggaacaacac tcaaccctat ctcgggctat   6840
tcttttgatt tataagggat tttgccgatt tcggaaccac catcaaacag gattttcgcc   6900
tgctggggca aaccagcgtg gaccgcttgc tgcaactctc tcagggccag gcggtgaagg   6960
gcaatcagct gttgcccgtc tcactggtga aaagaaaaac cacctgcg  cccaatacgc   7020 aaaccgcctc tccccgcgcg ttggccgatt cattaatgca gctggcacga caggtttccc   7080
gactggaaag cgggcagtga gcgcaacgca attaatgtga gttagctcac tcattaggca   7140
ccccaggctt tacactttat gcttccggct cgtatgttgt gtggaattgt gagcggataa   7200
caatttcaca caggaaacag ctatgaccat gattacgaag atcccctcac gctgccgcaa   7260
gcactcaggg cgcaagggct gctaaaggaa gcggaacacg tagaaagcca gtccgcagaa   7320
acggtgctga ccccgatga  atgtcagcta ctgggctatc tggacaaggg aaaacgcaag   7380
cgcaaagaga aagcaggtag cttgcagtgg gcttacatgg cgatagctag actgggcggt   7440
tttatggaca gcaagcgaac cggaattgcc agctggggcg ccctctggta aggttgggaa   7500
gccctgcaaa gtaaactgga tggctttctt gccgccaagg atctgatggc gcaggggatc   7560
aagatctgat caagagacag gatgaggatc gtttcgcatg attgaacaag atggattgca   7620
cgcaggttct ccggccgctt gggtggagag gctattcggc tatgactggg cacaacagac   7680
aatcggctgc tctgatgccg ccgtgttccg gctgtcagcg caggggcgcc cggttctttt   7740
tgtcaagacc gacctgtccg gtgccctgaa tgaactgcag gacgaggcag cgcggctatc   7800
gtggctggcc acgacgggcg ttccttgcgc agctgtgctc gacgttgtca ctgaagcggg   7860
aagggactgg ctgctattgg gcgaagtgcc ggggcaggat ctcctgtcat ctcaccttgc   7920
```

```
tcctgccgag aaagtatcca tcatggctga tgcaatgcgg cggctgcata cgcttgatcc    7980
ggctacctgc ccattcgacc accaagcgaa acatcgcatc gagcgagcac gtactcggat    8040
ggaagccggt cttgtcgatc aggatgatct ggacgaagag catcaggggc tcgcgccagc    8100
cgaactgttc gccaggctca aggcgcgcat gcccgacggc gaggatctcg tcgtgaccca    8160
tggcgatgcc tgcttgccga atatcatggt ggaaaatggc cgcttttctg gattcatcga    8220
ctgtggccgg ctgggtgtgg cggaccgcta tcaggacata gcgttggcta cccgtgatat    8280
tgctgaagag cttggcggcg aatgggctga ccgcttcctc gtgctttacg gtatcgccgc    8340
tcccgattcg cagcgcatcg ccttctatcg ccttcttgac gagttcttct gagcgggact    8400
ctggggttcg aaatgaccga ccaagcgacg cccaacctgc catcacgaga tttcgattcc    8460
accgccgcct tctatgaaag gttgggcttc ggaatcgttt tccgggacgc cggctggatg    8520
atcctccagc gcggggatct catgctggag ttcttcgccc accccagctt caaaagcgct    8580
ct                                                                   8582
```